United States Patent
Vastra et al.

(10) Patent No.: US 6,992,199 B2
(45) Date of Patent: Jan. 31, 2006

(54) METHOD FOR SULPHONYLATING A HYDROXYLATED ORGANIC COMPOUND

(75) Inventors: Johann Vastra, Serezin Du Rhone (FR); Laurent Saint-Jalmes, Meyzieu (FR)

(73) Assignee: Rhodia Chimie, Boulogne Billancourt (FR)

( * ) Notice: Subject to any disclaimer, the term of this patent is extended or adjusted under 35 U.S.C. 154(b) by 0 days.

(21) Appl. No.: 10/398,061

(22) PCT Filed: Oct. 2, 2001

(86) PCT No.: PCT/FR01/03040

§ 371 (c)(1),
(2), (4) Date: Aug. 11, 2003

(87) PCT Pub. No.: WO02/28826

PCT Pub. Date: Apr. 11, 2002

(65) Prior Publication Data

US 2004/0024257 A1    Feb. 5, 2004

(51) Int. Cl.
*C07F 9/02*    (2006.01)
(52) U.S. Cl. .................. 554/88; 560/715; 560/735; 560/840; 570/123; 570/127; 570/134
(58) Field of Classification Search ............... 570/123, 570/127, 134; 568/700, 715, 735, 840; 554/80
See application file for complete search history.

(56) References Cited

FOREIGN PATENT DOCUMENTS

EP    0 200 657    11/1986

OTHER PUBLICATIONS

WPIDS Abstr. of JP-51/55843, 1993.*
D. Prescher, et al. "Various synthetic approaches to fluoroalkyl p-nitrophenyl ethers"-Journal of Fluorine Chemistry, vol. 79, No. 2, Aug. 1, 1996, pp. 145-148, XP004069916.
G.A.Glah, et al.: "Preparative carbocation chemistry; VIII. Isolation and sulphonylation ability of sluphonylhalide-antimony pentahalides complexes" No.: 5, (May 1974), pp. 342-343, XP002169199. The whole document.
G.A.Glah, et al.: Stable carbonium ionsCXVI. Sulphonylpentafluoride complexes and . . . Journal of Organic Chemestry, vol. 35, No. 11 (Nov. 1970), pp. 3925-3928, XP002169198. The whole document.
International Search Report.

* cited by examiner

*Primary Examiner*—Deborah D. Carr

(57) ABSTRACT

The invention concerns a method for sulphonylating a hydroxylated organic compound. The invention concerns in particular aliphatic hydroxylated compounds and more particularly those which comprise on their aliphatic chain, an electroattractive group. The method for sulphonylating a hydroxylated organic compound is characterised in that it consists in reacting said compound, with a sulphonylating agent, in the presence of a sufficient amount of a Lewis acid.

36 Claims, No Drawings

METHOD FOR SULPHONYLATING A HYDROXYLATED ORGANIC COMPOUND

The present invention relates to a process for sulphonylating a hydroxylated organic compound. More particularly, the invention relates to aliphatic type hydroxylated compounds, more particularly those comprising an electron-attracting group in their aliphatic chain.

Preferably, the invention is applicable to perfluorinated aliphatic alcohols, in particular 2,2,2-trifluoroethanol.

Crossland et al. have shown that 2,2,2-trifluoroethylnethanesulphonate, abbreviated to "TFEMes" for simplicity, can be prepared by reacting 2,2,2-trifluoroethanol with mesyl chloride in the presence of a base such as triethylamine and in an organic solvent, namely dichloromethane.

The disadvantage with that process is that it is difficult to scale up to an industrial level as it results in poor productivity because of the extremely dilute reaction medium, and it also results in highly polluting discharges due to the presence of large quantities of ammonium salt.

The aim of the present invention is to provide a process that can overcome the disadvantages cited above.

We have now discovered, and this forms one aspect of the present invention, a process for sulphonylating a hydroxylated organic compound, characterized in that it consists of reacting said compound with a sulphonylating agent in the presence of an effective quantity of a Lewis acid.

In the present text, the term "Lewis acid" means a compound comprising a metal or metalloid cation that is an electron pair acceptor, which reacts with the sulphonylating agent rather than with the hydroxylated organic compound.

Regarding the choice of metal or metalloid cation, reference should be made to the "hard" and "soft" classification defined by R PEARSON in the Journal of Chem. Ed. 45, pages 581–587 (1968).

Borderline or the like metal or metallic cations are used, the term "borderline" being used as defined in the reference cited above.

The term "borderline" as used in the present invention means not only metal or metalloid cations classified as borderline, but also all those classified as hard or soft with the exception of very hard and very soft cations.

The term "hard cation" defines an electron-accepting atom which may be large or small and has a large positive charge which does not contain unpaired electrons in its valency orbital. They are generally small cations with a high oxidation number which do not have readily removable electrons.

Examples of very hard cations that can be cited are $B^{3+}$, $Mg^{2+}$, $Al^{3+}$, $Si^{4+}$, $Ti^{4+}$, $Mn^{2+}$, $Fe^{3+}$, $Zr^{4+}$ and $La^{3+}$.

The term "soft cation" means an electron-accepting atom which may be large or small and which has a small positive charge, which contains unpaired electrons (p or d) in the valency orbital. They are generally large cations with a low oxidation number with readily removable electrons.

Examples of very soft cations that can be mentioned are $Cu^+$, $Ag^+$, $Hg^+$.

Regarding the choice of a borderline cation as defined in the invention, reference should be made to the literature, in particular to the article by TSE-LOK HO [Chemical Reviews 75, n°1, pp 1–20 (1975)].

The borderline cation employed in the process of the invention has an oxidation number of at least +2, preferably +3, +4 or +5.

Suitable metal or metalloid cations that can be cited in particular are those of metal or metalloid elements from groups (IIb), (IVb), (Vb) and (VIb) from the periodic table.

In the present text, a reference to the periodic table will refer to that published in the Bulletin de la Société Chimique de France, n°1 (1966).

Particular examples of cations suitable for use in the process of the invention that can be cited are those from group (IIb), zinc; group (IVb), tin; group (Vb), antimony, bismuth; group (VIb), tellurium.

Preferred cations from those cited above are $Zn^{2+}$, $Sn^{2+}$, $Sn^{4+}$, $Sb^{5+}$, $Bi^{3+}$, $Te^{4+}$, and still more preferably $Sb^{5+}$.

The nature of the anions bonded to said cations allows the hardness or softness of the cation to be adjusted.

Hard anions, in particular $SO_4^{2-}$, $CH_3COO^-$, $C_6H_5COO^-$, $CH_3SO_3^-$, $CF_3SO_3^-$, $CF_3C_6H_4SO_3^-$ or borderline anions such as $Cl^-$, $Br^-$, $NO_2^-$ or $SO_3^{2-}$ can be mentioned.

Preferred anions from those cited above are $Cl^-$ and $Br^-$.

More specific examples of Lewis acids that can be mentioned are organic salts such as the acetate, propionate, benzoate, methanesulphonate, trifluoromethanesulphonate of metal or metalloid elements from said groups from the periodic table.

Regarding the inorganic salts, the chloride, bromide, iodide, sulphate, oxide and analogous products of the metal or metalloid elements from said groups can be cited.

Preferably, metal halides are selected, more particularly antimony (V), tin (II) or (IV), zinc (II), bismuth (III) or tellurium (IV) chloride or bromide.

It is possible to generate a halide in situ and thus, any compound of the elements cited above can be used, provided that it is associated with a source of a halogen.

The metal can be used in any form. They can be supplied in the form of the metal or the oxide or in the salt form, either a simple or double salt, mineral or organic. It is possible to use a mineral salt, preferably a nitrate, sulphate, oxysulphate, halide, oxyhalide, silicate, carbonate, oxalate or an organic salt, preferably the acetylacetonate; or an alcoholate, still more preferably the methylate or ethylate; carboxylate or still more preferably, the acetate.

Regarding the source of the halogen, any compound can be used which can supply halogen ions that can generate the metal or metalloid halide in situ.

Examples of halogen sources that can be cited are the molecular form of the halogen; any mineral or organic acid halide, more particularly of aliphatic carboxylic acids; and any mineral or organic metal or metalloid salt that can generate a halogenated form.

More specific examples that can be mentioned include the chloride or bromide; hydrochloric acid, hydrobromic acid; acetyl chloride; silicon chloride $SiCl_4$, halogenosilanes such as $Me_3SiCl$, $Me_2SiCl_2$, $MeSiCl_3$, $PhMe_2SiCl$, chlorides of phosphorus $PCl_5$ or $PCl_3$, and sulphur chloride $SCl_2$.

Depending on the physical form of the Lewis acid employed, catalysis can be homogeneous or heterogeneous.

If it is liquid or soluble in a solvent, generally water, it can be used in a supported form by depositing it on a mineral or organic support. To this end, the support can be selected from metal oxides such as aluminium, silicon, titanium and/or zirconium oxides, clays, and more particularly kaolin, talc or montmorillonite, or from charcoal, optionally activated by a known treatment with nitric acid, acetylene black or organic polymers, for example the polyvinyl polymers polyvinyl chloride (PVC), PVDC (polyvinylidene chloride), or polystyrene polymers that can be functionalized with nitrile functions, or polyacrylic polymers (in particular polyacrylonitrile).

The support can have any form, for example a powder, beads, granules, extrudates, etc.

The supported catalyst can be prepared using techniques that are known to the skilled person.

To prepare the supported catalyst for use in the process of the present invention, conventional techniques for preparing supported metallic catalysts can be used that are known per se. Reference can in particular be made to the preparation of the different catalysts described in "Catalyse de contact: conception, preparation et mise en oeuvre des catalyseurs industrials" [Contact catalysis: design, preparation and use of industrial catalysts], J F LEPAGE, Edition Technip (1978).

The catalyst can, for example, be prepared by introducing a support into a solution prepared by dissolving at least one suitable compound of the selected element(s); the active element or elements is/are deposited on the support by distilling off the solvent, usually water, and the contact mass obtained is then dried.

In a conventional preparation mode, the compounds supplying the active elements are deposited on the support by precipitating the compounds in a manner that is known per se and then drying the contact mass.

In the description, the term "catalyst" means the catalyst constituted by the Lewis acid, or the supported catalyst The amount of active phase represents 5% to 100% of the weight of the catalyst. In a supported catalyst, it represents 5% to 50%, preferably 5% to 20% by weight of the catalyst.

The catalysts can have different forms as used in the process of the invention: a powder, a formed product such as granules (for example extrudates or beads), or pellets, obtained by extrusion, moulding, compacting or any other known process.

Regarding the reagent employed, the hydroxylated organic compound is a compound with low nucleophilicity. It has this characteristic with the proviso that at least one electron-attracting group is present that is sufficiently close to the hydroxyl group to deactivate it. The electron-attracting group can be present on the linear or cyclic, saturated or unsaturated hydrocarbon chain carrying the hydroxyl group or it can be present on an aromatic carbocycle or heterocycle carried by a carbon atom carrying or close to (preferably in the α or β position) the atom carrying the hydroxyl group.

More precisely, it has formula (I):

$$R_1\text{—}O\text{—}H \qquad (I)$$

in which formula (I):

$R_1$ represents a hydrocarbon group substituted with at least one electron-attracting group (G), containing 1 to 40 carbon atoms which may be a linear or branched, saturated or unsaturated acyclic aliphatic group; a monocyclic or polycyclic, saturated or unsaturated or aromatic carbocyclic or heterocyclic group; or a concatenation of said groups.

More particularly, the electron-attracting group (G) is one of the following atoms or groups:

an acyl group containing 2 to 20 carbon atoms, preferably acetyl;

a group with formula:
—X
—$CX_3$
—$CF_2$—$CF_3$;
—$[CF_2]_p$—$CF_3$;
—$C_pH_aF_b$;
—COOM;
—$COOR_3$;
—CHO;
—$SO_3$-M;
—$SO_3$—$R_3$;
—$SO_2$—$R_3$;
—SO—$CF_3$;
—$SO_2$—$CF_3$;
—S—$CF_3$;
—$NO_2$;
—CN;
—N═$C(R_3)_2$;
—NH—CO—$R_3$;
—$N^+(R_3)_3$;
—$P(O)(OR_3)_2$;
$Si(R_3)_3$ in which formulae, groups $R_3$, which may be identical or different, represent a hydrogen atom or a linear or branched, saturated or unsaturated alkyl group containing 1 to 20 carbon atoms; X represents a halogen atom, preferably a chlorine, bromine or fluorine atom; M represents an alkali metal atom, preferably sodium or potassium; p represents a number from 1 to 10, b represents a number from 3 to 21 and a+b—2p+1.

When group (G) is carried by an aromatic ring, this group can be substituted for a hydrogen atom or it can be bonded to the cycle via a group in the manner of —$R_2$-G; $R_2$ represents a covalent bond or a divalent, linear or branched, saturated or unsaturated hydrocarbon group containing 1 to 4 carbon atoms such as methylene, ethylene, propylene, isopropylene or isopropylidene.

Preferred groups from those cited above are halogen atoms, the trifluoromethyl group and the nitrile or nitro group.

More precisely, $R_1$ represents a hydrocarbon group containing 1 to 20 carbon atoms, which may be a linear or branched, saturated or unsaturated acyclic aliphatic group; a monocyclic or polycyclic, saturated, unsaturated or aromatic carbocyclic or heterocyclic group; or a linear or branched, saturated or unsaturated aliphatic group carrying a cyclic substituent.

Preferably, $R_1$ represents a linear or branched, saturated acyclic aliphatic group preferably containing 1 to 12 carbon atoms, more preferably 1 to 4 carbon atoms, The invention does not exclude the presence of a single unsaturated bond on the hydrocarbon chain such as one or more double bonds, which may or may not be conjugated, or a triple bond.

The hydrocarbon chain can optionally be interrupted by a heteroatom (for example oxygen or sulphur) or by a functional group, provided that it does not react; the group —CO— can in particular be cited.

The hydrocarbon chain can optionally carry one or more substituents (for example halogen, ester, aldehyde) provided that they do not interfere with the sulphonylation reaction.

The linear or branched, saturated or unsaturated, acyclic aliphatic group can optionally carry a cyclic substituent. The term "cycle" means a saturated, unsaturated or aromatic carbocyclic or heterocyclic cycle.

The acyclic aliphatic group can be bonded to the cycle via a covalent bond, a heteroatom or a functional group such as oxy, carbonyl, sulphonyl, etc.

Examples of cyclic substituents that can be envisaged are cycloaliphatic, aromatic or heterocyclic substituents, in particular cycloaliphatic substituents containing 6 carbon atoms in the cycle or benzenic compounds, said cyclic substituents themselves optionally carrying any substituent provided that they do not interfere with the reactions occurring in the process of the invention. Particular mention can be made of alkyl or alkoxy groups containing 1 to 4 carbon atoms.

More particular examples of aliphatic groups carrying a cyclic substituent are aralkyl groups containing 7 to 12 carbon atoms, in particular benzyl or phenylethyl.

In formula (I), $R_1$ can also represent a saturated or unsaturated carbocyclic group preferably containing 5 or 6 carbon atoms in the cycle; a saturated or unsaturated heterocyclic group containing 5 or 6 carbon atoms in the cycle 1 including 1 or 2 heteroatoms such as nitrogen, sulphur or oxygen atoms; a monocyclic aromatic carbocyclic or heterocyclic group, preferably phenyl or pyridyl, or a condensed or non-condensed polycyclic group, preferably naphthyl.

If $R_1$ includes a cycle, it can also be substituted. The number of substituents is generally at most 4 per cycle, but is usually 1 or 2.

Preferably, $R_1$ is a linear or branched alkyl group containing 1 to 12 carbon atoms, or the phenyl group.

More particularly, the process of the invention is applicable to fluorinated and perfluorinated aliphatic alcohols with formula (Ia):

$$R_1-O-H \quad \text{(Ia)}$$

in which formula (Ia), $R_1$ represents a fluorinated or perfluorinated alkyl chain containing 1 to 10 carbon atoms and 1 to 21 fluorine atoms, preferably 3 to 21 fluorine atoms.

The process of the invention is particularly applicable to compounds with formula (I) such as 2,2,2-trifluoroethanol, 2,2-difluoroethanol, 1,1-difluoroethanol, pentafluoroethanol, hexafluoroisopropanol, pentafluorophenol, p-nitrophenol and p-trifluoromethylphenol.

The sulphonylating agent is a compound comprising at least one $-SO_2R_4$ type sulphonyl group in which $R_4$ represents a hydrocarbon group containing 1 to 20 carbon atoms.

More particularly, it has the following formula (II):

$$Z-\overset{\overset{O}{\|}}{\underset{\underset{O}{\|}}{S}}-R_4 \quad \text{(II)}$$

in which formula (II):
$R_4$ represents a hydrocarbon group containing 1 to 20 carbon atoms;
Z represents:
  a hydroxyl group or a halogen atom, preferably a chlorine or bromine atom;
  a group $-O-SO_2-R'_4$, in which $R'_4$, which may be identical to or different from $R_4$, has the meaning given for $R_4$.

Preferred sulphonylating agents have formula (II) in which Z represents a chlorine or bromine atom.

In formula (II), $R_4$ more particularly represents:
an alkyl group containing 1 to 10 carbon atoms, preferably 1 to 4 carbon atoms, more preferably a methyl or ethyl group, optionally carrying a halogen atom, a $CF_3$ group or an ammonium group $N(R_5)_4$, where groups $R_5$, which may be identical or different, representing an alkyl group containing 1 to 4 carbon atoms;
a cycloalkyl group containing 3 to 8 carbon atoms, preferably a cyclohexyl group;
an aryl group containing 6 to 12 carbon atoms, preferably a phenyl group optionally carrying an alkyl group containing 1 to 10 carbon atoms, preferably 1 to 4 carbon atoms and more preferably a methyl or ethyl group, a halogen atom, a $CF_3$ group or a $NO_2$ group;
a group $CX_3$ in which X represents a fluorine, chlorine or bromine atom;
a group $CF_2-CF_3$;
a group $C_pH_aF_b$ in which p represents a number from 1 to 10, b a number from 3 to 21 and $a+b=2p+1$.

Preferred sulphonylating agents have formula (I) in which the group $-SO_2-R_4$ represents:
tosyl groups (p-toluenesulphonyl) $-SO_2-C_6H_4-CH_3$;
brosyl groups (p-bromobenzenesulphonyl) $-SO_2-C_6H_4-Br$;
nosyl groups (p-nitrobenzenesulphonyl) $-SO_2-C_6H_4-NO_2$;
mesyl groups (methanesulphonyl) $-SO_2-CH_3$;
betyl groups (ammonioalkanesulphonyl) $-SO_2(CH_2)_nNMe_3^+$ where n is in the range 0 to 6;
triflyl groups (trifluoromethanesulphonyl) $-SO_2-CF_3$;
nonaflyl groups (nonafluorobutanesulphonyl) $-SO_2-C_4F_9$;
tresyl groups (2,2,2-trifluoroethanesulphonyl) $-SO_2-CH_2-CF_3$.

Preferred examples of sulphonylating agents that can be employed in particular are:
triflic anhydride;
methanesulphonyl chloride;
trifluormethanesulphonyl chloride;
benzenesulphonyl chloride;
p-toluenesulphonyl chloride.

In accordance with the process of the invention, a sulphonylated organic compound is obtained by reacting a hydroxylated organic compound preferably with formula (I) with a sulphonylating agent preferably with formula (II), in the presence of a Lewis acid comprising a metal or metalloid cation M as defined above with an oxidation number n and a counter-ion to the metal cation which is symbolized by Y.

The catalytic entity involved in the process of the invention is represented by formulae (IV):

$$\left[\overset{O}{\underset{R_4}{\overset{\|}{S}}}\overset{O\rightarrow MY_{n-1}}{\underset{Z}{}}\right]_x^+ Y^- \quad \text{or} \quad \left[\overset{O}{\underset{R_4}{\overset{\|}{S}}}\overset{O}{\underset{+}{}}\right]^+ MY_nZ^- \quad \text{(IV)}$$

in which formulae:
$R_4$ and Z have the meanings given above;
M represents the metal or metalloid with oxidation number n;
Y represents the counter-ion to the cation $M^{n+}$.

More precisely, the present invention encompasses the catalytic entity with formulae (IVa) as novel products:

$$\left[\overset{O}{\underset{R_4}{\overset{\|}{S}}}\overset{O\rightarrow SbCl_4}{\underset{Cl}{}}\right]_x^+ Cl^- \quad \text{or} \quad \left[\overset{O}{\underset{R_4}{\overset{\|}{S}}}\overset{O}{\underset{+}{}}\right]^+ SbCl_6^- \quad \text{(IVa)}$$

in which formulae:
$R_4$ has the meaning given above.

In the process of the invention, the reaction between the hydroxylated compound and the sulphonylating agent is carried out in the liquid phase in the presence or absence of an organic solvent.

In a variation, the process of the invention consists of carrying out the reaction in an organic solvent.

A number of criteria govern the choice of solvent.

It must be inert under the conditions of the process of the invention and must have a boiling point that is higher than the reaction temperature.

Preferably, an aprotic and low polarity organic solvent is used.

Particular examples of solvents that are suitable for use in the present invention that can be cited are halogenated or non-halogenated aliphatic or aromatic hydrocarbons.

More particular examples of aliphatic hydrocarbons that can be cited are paraffins such as hexane, heptane, octane, nonane, decane, undecane, dodecane, tetradecane or cyclohexane and aromatic hydrocarbons, more particularly aromatic hydrocarbons such as benzene, toluene, xylenes, cumene, or petroleum cuts constituted by a mixture of alkylbenzenes in particular Solvesso® type cuts.

More particular examples of aliphatic or halogenated hydrocarbons that can be mentioned include perchlorinated hydrocarbons such as tetrachloromethane, tetrachloroethylene and hexachloroethane; partially chlorinated hydrocarbons such as dichloromethane, chloroform, 1,2-dichloroethane, 1,1,1-trichloroethane, 1,1,2,2-tetrachloroethane, pentachloroethane, trichloroethylene, 1-chlorobutane, 1,2-dichlorobutane; monochlorobenzene, 1,2-dichlorobenzene, 1,3-dichlorobenzene, 1,4-dichlorobenzene, 1,2,4-trichlorobenzene or mixtures of different chlorobenzenes; bromoform, bromoethane or 1,2-dibromoethane; monobromobenzene or mixtures of monobromobenzene with one or more dibromobenzenes; and 1-bromonapthalene.

It is also possible to use a mixture of organic solvents.

Preferred solvents are dichloromethane and toluene.

As mentioned above, the hydroxylated compound is reacted with a sulphonylating agent, optionally in the presence of a reaction solvent as defined and in the presence of a Lewis acid type catalyst.

The ratio between the number of moles of sulphonylating agent and the number of moles of hydroxylated compound can be in the range 0.9 to 2, and is preferably in the range 1.0 to 1.2.

The quantity of catalyst used in the process of the invention can vary widely. It can represent 0.01% to 20%, preferably 0.05% to 10% and more preferably 0.1% to 2%, by weight with respect to the hydroxylated compound employed.

When an organic solvent is employed, it is used in a quantity that is generally selected so that the concentration of the product obtained is in the range 10% to 60%, preferably in the range 20% to 30%.

The temperature at which the sulphonylation reaction is carried out depends on the reactivity of the starting substrate and on that of the sulphonylating agent.

It is between 20° C. and 150° C., preferably in the range 70° C. to 100° C.

Generally, the reaction is carried out at atmospheric pressure, but lower or higher pressures are also suitable. Autogenous pressure is employed when the reaction temperature is higher than the boiling point of the reagents and/or products.

In a preferred variation of the process of the invention, it is carried out in a controlled inert gas atmosphere. A rare gas atmosphere can be established, preferably argon, but it is cheaper to use nitrogen.

From a practical viewpoint, the process can be carried out batchwise or continuously.

In a first variation, the sulphonylating agent and the Lewis acid type catalyst are charged.

After bringing the reagents into contact, the reaction mixture is heated to the desired temperature with stirring.

The hydroxylated compound is then added, preferably slowly.

Stirring is continued until all of the reagents have been consumed, as monitored by an analytical method, for example gas chromatography.

At the end of the reaction, a liquid phase that comprises the sulphonylated compound is obtained; it can be recovered conventionally, for example by distillation or crystallization.

After separating the sulphonylated compound by distillation, a distillation liquor is obtained comprising the catalyst and which can be recycled a number of times.

It is also possible to separate out the catalyst at the end of the reaction. If it is insoluble, it can be separated using a solid/liquid separation technique, preferably by filtering.

In the case of a soluble catalyst, it is eliminated by treating the medium with a complexing agent, for example tartaric acid or sodium carbonate.

When preparing 2,2,2-trifluoroethylmethanesulphonate from 2,2,2-trifluoroethanol and mesyl chloride, the hydrochloric acid formed is trapped in a basic column, preferably caustic soda, then the product formed is recovered by distillation.

In the second variation, the reaction is carried out continuously in a tube reactor comprising the solid catalyst disposed in a fixed bed.

The hydroxylated compound and the sulphonylating agent can be introduced separately or mixed in the reactor.

They can also be introduced into a solvent as mentioned above.

The liquid phase obtained is treated as described above.

A sulphonylated compound with formula (III) is obtained:

(III)

in which formula (III), $R_1$ and $R_4$ have the meanings given above.

The compound with formula (III) can be used as an intermediate product for the preparation of ether-oxides.

Compound (III) can bind a group $R_1$ to a hydroxylated organic compound (in particular a hydroxylated aromatic compound) which can be represented by the formula (V);

(V)

in which formula, $R_6$ has the meanings given for $R_1$, without necessitating the presence of an electron-attracting group.

In a further aspect, the invention provides a process for preparing an ether-oxide with formula (VI):

(VI)

in which formula, $R_6$, which may be identical to or different from $R_1$, has the meanings given for $R_1$ without the necessity for the presence of an electron-attracting group, characterized in that it consists of preparing a compound with formula (III) obtained in accordance with the process of the invention then reacting the product obtained with a hydroxylated compound with formula (V) in the presence of a base.

The invention can produce symmetrical ether-oxides if $R_6$ is identical to $R_1$ or asymmetrical ether-oxides if $R_6$ is different from $R_1$.

In accordance with the invention, a compound with formula (VI) is prepared in which $R_6$ represents an aromatic cycle and which has the following formula:

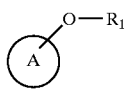

(VIa)

in which formula (VIa), $R_1$ has the meaning given above and A represents the residue of a cycle forming all or a portion of a monocyclic or polycyclic, aromatic carbocyclic or heterocyclic system.

The invention is particularly applicable to aromatic compounds with formula (VIa) in which A is a residue of a cyclic compound preferably containing at least 4 atoms in the cycle, which may be substituted, and representing at least one of the following cycles:
  a monocyclic or polycyclic aromatic carbocycle;
  a monocyclic or polycyclic aromatic heterocycle containing at least one of heteroatoms O, N or S;

Without limiting the scope of the invention, residue A, which may be substituted, can represent the residue:
  1°—of a monocyclic or polycyclic aromatic carbocyclic compound.
  The term "polycyclic carbocyclic compound" means:
    a compound constituted by at least 2 aromatic carbocycles and forming between them ortho- or ortho- and pericondensed systems;
    a compound constituted by at least 2 carbocycles one of which is aromatic and forming between them ortho- or ortho- and pericondensed systems.
  2°—of a monocyclic or polycyclic aromatic heterocyclic compound.
  The term "polycyclic heterocyclic compound" means:
    a compound constituted by at least 2 heterocycles containing at least one heteroatom in each cycle at least one of the two cycles being aromatic and forming between them ortho- or ortho- and pericondensed systems;
    a compound constituted by at least one hydrocarbon cycle and at least one heterocycle at least one of the cycles being aromatic and forming between them ortho- or ortho- and pericondensed systems.
  3°—of a compound constituted by a concatenation of cycles, as defined in paragraphs 1 and/or 2 bonded together via a covalent bond, via an alkylene or alkylidene group containing 1 to 4 carbon atoms, preferably a methylene or isopropylidene group or via an atom or groups such as oxygen, a carbonyl group or a carboxy group, etc. . . .

More particularly, residue A, which may be substituted, represents the residue:
  of an aromatic, carbocyclic monocyclic compound such as benzene, for example;
  of an aromatic condensed polycyclic compound such as naphthalene, for example;
  of an aromatic carbocyclic non condensed polycyclic compound such as phenoxybenzene;
  of a partially aromatic carbocyclic condensed polycyclic compound such as tetrahydronaphthalene, 1,2-methylene dioxybenzene, for example;
  of a partially aromatic, carbocyclic non condensed polycyclic compound such as cyclohexylbenzene, for example;
  of an aromatic heterocyclic monocyclic compound such as pyridine, furan or thiophene;
  of a partially heterocyclic, aromatic condensed polycyclic compound such as quinoline, indole or benzofuran;
  of a partially heterocyclic, aromatic non condensed polycyclic compound such as phenylpyridines or naphthylpyridines;
  of a partially heterocyclic, partially aromatic, condensed polycyclic compound such as tetrahydroquinoline, for example;
  of a partially heterocyclic, partially aromatic, non condensed polycyclic compound such as cyclohexylpyridine, for example.

The invention does not exclude the presence of a substituent on the cycle of any nature provided that it does not interfere with the reaction. Alkyl or alkoxy groups containing 1 to 4 carbon atoms can be cited, inter alia.

The reaction of the compound with formula (V) and compound with formula (III) is an O-alkylation reaction which is carried out in the presence of a base.

Thus, the process of the invention employs a base which may be mineral or organic.

Preferably, a strong base is selected, i.e., a base with a pKa of 10 or more: the pKa is defined as the co logarithm of the dissociation constant of the conjugated acid measured in an aqueous medium at 25° C.

Mineral bases such as alkali metal salts are particularly suitable for use in the process of the invention, such as an alkali metal hydroxyide, which can be sodium or potassium hydroxide; or an alkali metal carbonate, preferably potassium carbonate.

It is also possible to use a quaternary ammonium hydroxide.

Examples of quaternary ammonium hydroxides that are preferably employed are tetraalkylammonium or trialkylbenzylammonium hydroxides wherein the alkyl groups, which may be identical or different, represent a linear or branched alkyl chain containing 1 to 12 carbon atoms, preferably 1 to 6 carbon atoms. Preferably, tetramethylammonium hydroxide, tetraethylammonium hydroxide, tetrabutylammonium hydroxide or trimethylbenzylammonium hydroxide are used.

A metal alcoholate can also be used, for example sodium or potassium methylate or potassium tert-butylate.

For reasons of economy, sodium hydroxide or potassium carbonate is used as the selected base.

The concentration of basic starting solution is not critical. The alkali metal hydroxide solution is employed at a concentration that is generally in the range 10% to 50% by weight.

The quantity of base introduced into the reaction medium is such that the ratio between the number of moles of base, expressed as OH⁻, and the number of moles of compound (V) is in the range 1 to 2, preferably in the range 1 to 1.5.

The reaction is carried out in the presence of an organic solvent, preferably a polar organic solvent.

Examples of polar aprotic organic solvents that can also be employed in the process of the invention that can more particularly be cited are nitro compounds, for example nitromethane, nitroethane, 1-nitropropane, 2-nitropropane or mixtures thereof, or nitrobenzene; aliphatic or aromatic nitrites such as acetonitrile, propionitrile, benzonitrile or benzyl cyanide; linear or cyclic carboxamides such as N,N-dimethylacetamide (DMAC), N,N-diethylacetamide, dimethylformamide (DMF), diethylformamide or 1-methyl-2-pyrrolidone (NMP); dimethylsulphoxide (DMSO); tetramethylenesulpholane (sulpholane); and hexamethylphosphotriamide (HMPT).

The organic solvent can also be an aliphatic, cycloaliphatic or aromatic ether-oxide, more particularly dipropyl oxide, diisopropyl oxide, dibutyl oxide, methyltertiobutyl ether, ethylene glycol dimethylether (glyme), diethylene glycol dimethylether (diglyme); phenyl oxide; dioxane, or tetrahydrofuran (THF).

Preferred solvents are DMAC and DMF.

It is also possible to use a mixture of organic solvents.

The different reagents and substrates are used in the quantities defined below.

The concentration of compound with formula (V), preferably (Va), employed in the solvent can vary widely. Generally, the concentration of said compound is in the range 20% to 30% of the solvent weight.

The basification reaction is carried out between 0° C. and 60° C., preferably between 0° C. and 20° C.

It is generally carried out at atmospheric pressure.

From a practical viewpoint, the salt of the compound with formula (V) is prepared by reacting it with the base.

The water formed is eliminated and then the sulphonylated compound is added.

The O-alkylation reaction is carried out between 60° C. and 160° C., preferably between 120° C. and 140° C.

The O-alkylated compound with formula (VI) is obtained.

The reaction solvent is evaporated off and the product obtained is recovered conventionally, for example by distillation or crystallization.

Examples of implementations of the process of the invention will now be given by way of non-limiting illustration.

$$\text{Yield } (RR) = \frac{\text{number of moles of sulphonylated compound formed}}{\text{number of moles of hydroxylated compound introducted}} \%$$

EXAMPLE 1

Preparation of 2,2,2-trifluoroethylmethanesulphonate (TFEMes) in a Semi-Continuous Process The following were successively charged into a reactor: 600 g of mesyl chloride (CMS, reference compound) and 24 g of $SbCl_5$.

The mixture was stirred and heated to 75–85° C.

552 g of 2,2,2-trifluoroethanol (TFE) was then slowly added, keeping the temperature between 75° C. and 80° C.

The reaction mixture was stirred for about 2 hours more after adding the TFE.

The crude reaction medium was then cooled to ambient temperature before being distilled under reduced pressure (20–50 mbars, boiling point of TFEMes=99° C./35 mm Hg).

After distillation, 828 g of TFEMes was obtained, giving a yield of 89%.

EXAMPLE 2

Preparation of 2,2,2-trifluoroethylmethanesulphonate (TFEMes) in a Semi-Continuous Process The following were successively charged into a reactor: 600 z of 2,2,2-trifluoroethanol (TFE, reference compound) and 90 g of $ZnCl_2$.

The mixture was stirred and heated to 75–85° C. 738 g of mesyl chloride (CMS) was then slowly added, keeping the temperature between 75° C. and 85° C. for about 13 hours.

The crude reaction medium was then cooled to ambient temperature before being distilled under reduced pressure (20–50 mbars, boiling point of TFEMes=99° C./35 mm Hg).

After distillation, 714 g of TFEMes was obtained, giving a yield of 67%.

EXAMPLE 3

Preparation of 2,2,2-trifluoroethylmethanesulphonate (TFEMes) in a Batch Process The following were successively charged into a reactor: 750 g of mesyl chloride (CMS), 96 g of $TeCl_4$ and 600 g of and 24 g of 2,2,2-trifluoroethanol (TFE, reference compound).

The mixture was stirred and heated to 75–85° C. for about 9 hours.

The crude reaction medium was then cooled to ambient temperature before being distilled under reduced pressure (20–50 mbars, boiling point of TFEMes=99° C./35 mm Hg).

After distillation, 450 g of TFEMes was obtained, giving a yield of 42%.

EXAMPLE 4

Preparation of Phenyl 2,2,2-trifluoroethyl Oxide

Starting from 2,2,2-trifluoroethylnethanesulphonate (TFEMes) prepared using any of Examples 1–3, ethers such as phenyl oxide and 2,2,2-trifluoroethyl can be obtained as follows:

600 g of phenol (reference compound) was dissolved in 4920 g of dimethylacetamide (DMAC) in a reactor.

The solution obtained was heated to 50° C. then 1.3 g of an aqueous 50% by weight KOH solution was slowly added.

The mixture was kept at 60° C. for about 30 minutes after adding the KOH solution.

The water formed was evaporated off under reduced pressure.

1236 g of TFEMes was then slowly added (about 2 hours) to the reaction mixture, keeping the temperature of the reaction mixture between 120° C. and 140° C.

Following addition, the temperature (120–140° C.) and stirring were maintained for about 3 hours.

The solvent was then distilled off under reduced pressure and the concentrate was taken up in 3600 g of water and 3000 g of toluene.

The organic phase was then washed with 3600 g of water, dried over $K_2CO_3$, filtered, and the solvents were evaporated off under reduced pressure.

The concentrate yielded 80–85% by weight of the expected product.

EXAMPLE 5

Preparation of 1,1,1,3,3,3-hexafluoroisopropylmethanesulphonate (HFIPMes) in a Batch Process The following were successively charged into a reactor: 600 g of mesyl chloride (CMS, reference compound), 24 g of $SbCl_5$ and 880 g of 1,1,1,3,3,3-hexafluoro-2-propanol (HFIP).

The mixture was stirred and heated to 55° C. for about 9 hours.

The crude reaction medium was then cooled to ambient temperature before being distilled under reduced pressure (20–50 mbars, boiling point of TFEMes=99° C./35 mm Hg).

After distillation, 1160 g of HFIPMes was obtained, giving a yield of 90%.

EXAMPLE 6

Preparation of 2,2,2-trichloroethylmethanesulphonate (TCEMes) in a Batch Process The following were successively charged into a reactor: 600 g of mesyl chloride (CMS, reference compound), 24 g of $SbCl_5$ and 783 g of 2,2,2-trichloroethanol (TCE).

The mixture was stirred and heated to 85–90° C. for about 8 hours.

The crude reaction medium was then assayed by gas chromatography with an internal reference, which indicated that the yield of TCEMes was 48%.

EXAMPLE 7

Preparation of 2,2-difluoroethylmethanesulphonate (DFEMes) in a Batch Process The following were successively charged into a reactor: 6 g of mesyl chloride (CMS, reference compound), 0.24 g of SbCls of and 4.3 g of 2,2,-difluoroethanol (DFE).

The mixture was stirred and heated to 80–85° C. for about 8 hours.

The crude reaction medium was then assayed by gas chromatography with an internal reference, which indicated that the yield of DFEMes was 11%.

EXAMPLE 8

Preparation of 2-fluoroethylmethanesulphonate (MFEMes) in a Batch Process

The following were successively charged into a reactor: 6 g of mesyl chloride (CMS, reference compound), 0.24 g of $SbCl_5$ of and 6 g of 3,3,3-trifluoropropanol (TFP).

The mixture was stirred and heated to 85–90° C. for about 8 hours.

The crude reaction medium was then assayed by gas chromatography with an internal reference, which indicated that the yield of MFEMes was 44%.

EXAMPLE 9

Preparation of 3,3,3-trifluoropropylmethanesulphonate (mNPMes) in a Batch Process The following were successively charged into a reactor: 6 g of mesyl chloride (CMS, reference compound), 0.24 g of $SbCl_5$ of and 7.3 g of 3-nitrophenol (mNP).

The mixture was stirred and heated to 85–90° C. for about 8 hours.

The crude reaction medium was then assayed by gas chromatography with an internal reference, which indicated that the yield of mNPMes was 34%.

The invention claimed is:

1. A process for sulphonylating a hydroxylated organic compound, comprising the step of reacting said compound with a sulphonylating agent in the presence of an effective quantity of a Lewis acid, wherein the sulphonylating agent is a compound comprising at least one —$SO_2R_4$ sulphonyl group wherein $R_4$ represents a hydrocarbon group containing 1 to 20 carbon atoms, and wherein the hydroxylated organic compound has at least one electron-attracting group that is sufficiently close to the hydroxyl group to deactivate it; the electron-attracting group optionally being present on the linear or cyclic, saturated or unsaturated hydrocarbon chain carrying the hydroxyl group or present on an aromatic carbocycle or heterocycle carried by a carbon atom carrying or close to that carrying the hydroxyl group.

2. A process according to claim 1, wherein the Lewis acid is a compound comprising a metal or metalloid cation that accepts electron pairs defined as "borderline" in the "hard-soft" classification.

3. The process according to claim 2, wherein the "borderline" cation employed has an oxidation number of at least +2.

4. The process according to claim 2, wherein the cation is a metal or metalloid cation of metallic or metalloid elements from groups (Iib), (Ivb), (Vb) and (Vib) of the periodic table.

5. The process according to claim 2, wherein the cation is $Zn^{2+}$, $Sn^{2+}$, $Sn^{4+}$, $Sb^{5+}$, $Bi^{3+}$, or $Te^{4+}$.

6. The process according to claim 5, wherein the cation is $Sb^{5+}$.

7. The process according to claim 1, wherein the Lewis acid is a compound comprising hard anions or borderline anions.

8. The process according to claim 1, wherein the Lewis acid is a compound comprising an anion selected from the group consisting of $SO_4^{2-}$, $CH_3COO^-$, $C_6H_5COO^-$, $CH_3SO_3^-$, $CF_3SO_3^-$, $CF_3C_6H_4SO_3^-$, $Cl^-$, $Br^-$, $NO_2^-$ and $SO_3^{2-}$.

9. The process according to claim 4, wherein the Lewis acid is an organic salt or an inorganic salt of said metal or metalloid elements.

10. The process according to claim 4, wherein the Lewis acid is an acetate, propionate, benzoate, methanesulphonate, trifluoromethanesulphonate, chloride, bromide, iodide, sulphate or oxide of said metal or metalloid elements.

11. The process according to claim 1, wherein the Lewis acid is antimony (V), tin (II) or (IV), zinc (II), bismuth (III) or tellurium (IV) chloride or bromide.

12. A process for sulphonylating a hydroxylated organic compound, comprising the step of reacting said compound with a sulphonylating agent in the presence of an effective quantity of a Lewis acid, wherein the sulphonylating agent is a compound comprising at least one —$SO_2R_4$ sulphonyl group wherein $R_4$ represents a hydrocarbon group containing 1 to 20 carbon atoms, and wherein the Lewis acid is deposited on a mineral or organic support.

13. The process according to claim 12, wherein the support is metal oxides, clays, charcoals, optionally activated by treatment with nitric acid, acetylene black, or organic polymers.

14. The process according to claim 13, wherein the support is aluminium oxides, silicon oxides, titanium oxides, zirconium oxides, kaolin, talc, montmorillonite, polyvinyl or polystyrene.

15. The process according to claim 12, wherein the hydroxylated organic compound has at least one electron-attracting group that is sufficiently close to the hydroxyl group to deactivate it; the electron-attracting group optionally being present on the linear or cyclic, saturated or unsaturated hydrocarbon chain carrying the hydroxyl group or present on an aromatic carbocycle or heterocycle carried by a carbon atom carrying or close to that carrying the hydroxyl group.

16. The process according to claim 1, wherein the hydroxylated organic compound has formula (I):

$$R_1\text{—O—H} \qquad (I)$$

wherein:
$R_1$ represents a hydrocarbon group substituted with at least one electron-attracting group (G), containing 1 to 40 carbon atoms, which is a linear or branched, saturated or unsaturated acyclic aliphatic group; a monocyclic or polycyclic, saturated or unsaturated or aromatic carbocyclic or heterocyclic group; or a concatenation of said groups.

17. The process according to claim 16, wherein the electron-attracting group (G) is:
an acyl group containing 2 to 20 carbon atoms;
an acetyl group;
—X
—CX$_3$
—CF$_2$—CF$_3$;
—[CF$_2$]$_p$—CF$_3$;
—C$_p$H$_a$F$_b$;
—COOM;
—COOR$_3$;
—CHO;
—SO$_3$-M;
—SO$_3$—R$_3$;
—SO$_2$—R$_3$;
—SO—CF$_3$;
—SO$_2$—CF$_3$;
—S—CF$_3$;
—NO$_2$;
—CN;
—N=C(R$_3$)$_2$;
—NH—CO—R$_3$;
—N$^+$(R$_3$)$_3$;
—P(O)(OR$_3$)$_2$;
Si(R$_3$)$_3$
wherein, groups R$_3$, which are identical or different, represent a hydrogen atom or a linear or branched, saturated or unsaturated alkyl group containing 1 to 20 carbon atoms; X represents a halogen atom; M represents an alkali metal atom; p represents a number from 1 to 10, b represents a number from 3 to 21 and a+b—2p+1.

18. The process according to claim 16, wherein R$_1$ represents:
a linear or branched acyclic aliphatic group;
an acyclic aliphatic group carrying a cyclic substituent, optionally substituted, bonded to the cycle via a covalent bond, a heteroatom or a functional group;
a saturated or unsaturated carbocyclic group containing 5 or 6 carbon atoms in the cycle; a saturated or unsaturated heterocyclic group containing 5 or 6 atoms in the cycle including 1 or 2 heteroatoms which are nitrogen, sulphur or oxygen atoms; a monocyclic aromatic carbocyclic or heterocyclic group, a phenyl or pyridyl, or a condensed or non condensed polycyclic group.

19. The process according to claim 12, wherein the hydroxylated organic compound has formula (I):

$$R_1\text{—O—H} \qquad (I)$$

wherein:
$R_1$ represents a hydrocarbon group substituted with at least one electron-attracting group (G), containing 1 to 40 carbon atoms, which is a linear or branched, saturated or unsaturated acyclic aliphatic group; a monocyclic or polycyclic, saturated or unsaturated or aromatic carbocyclic or heterocyclic group; or a concatenation of said groups, and wherein $R_1$ represents a linear or branched alkyl group containing 1 to 12 carbon atoms, whose hydrocarbon chain optionally being interrupted by a heteroatom or by a functional group or carrying a substituent.

20. The process according to claim 12, wherein the hydroxylated organic compound has formula (Ia):

$$R_1\text{—O—H} \qquad (Ia)$$

wherein $R_1$ represents a fluorinated or perfluorinated alkyl chain containing 1 to 10 carbon atoms and 1 to 21 fluorine atoms.

21. The process according to claim 12, wherein the hydroxylated organic compound is 2,2,2-trifluoroethanol, 2,2-difluoroethanol, 1,1-difluoroethanol, pentafluoroethanol, hexafluoroisopropanol, pentafluorophenol, p-nitrophenol or p-trifluoromethylphenol.

22. The process according to claim 1, wherein the sulphonylating agent is a compound with the following formula (II):

$$\underset{\underset{O}{\|}}{\overset{\overset{O}{\|}}{Z\text{—S—}R_4}} \qquad (II)$$

wherein:
R$_4$ represents a hydrocarbon group containing 1 to 20 carbon atoms; and Z represents a hydroxyl group, a halogen atom, a group —O—SO$_2$—R'$_4$, wherein R'$_4$, which is identical to or different from R$_4$, has the meaning given above for R4.

23. The process according to claim 22, wherein Z represents a chlorine or bromine atom.

24. The process according to claim 22, wherein R$_4$ represents:
an alkyl group containing 1 to 10 carbon atoms, which optionally carries a halogen atom, a CF3 group or an ammonium group N(R5)4, where groups R$_5$, which are identical or different, represent an alkyl group containing 1 to 4 carbon atoms;
a cycloalkyl group containing 3 to 8 carbon atoms;
an aryl group containing 6 to 12 carbon atoms, optionally carrying an alkyl group containing 1 to 10 carbon atoms, a halogen atom, a CF$_3$ group or a NO$_2$ group;
a group CX$_3$ in which X represents a fluorine, chlorine or bromine atom;
a group CF$_2$—CF$_3$;
a group C$_p$H$_a$F$_b$ in which p represents a number from 1 to 10, b a number from 3 to 21 and a+b=2p+1.

25. A process according to claim 22, wherein the group —SO$_2$—R$_4$ represents:
tosyl groups (p-toluenesulphonyl) —SO$_2$—C$_6$H$_4$—CH$_3$;
brosyl groups (p-bromobenzenesulphonyl) —SO$_2$—C$_6$H$_4$—Br;
nosyl groups (p-nitrobenzenesulphonyl) —SO$_2$—C$_6$H$_4$—NO$_2$;
mesyl groups (methanesulphonyl) —SO$_2$—CH$_3$;
betyl groups (ammonioalkanesulphonyl) —SO$_2$(CH$_2$)$_n$NMe$_3{}^+$ where n is in the range 0 to 6;
triflyl groups (trifluoromethanesulphonyl) —SO$_2$—CF$_3$;
nonaflyl groups (nonafluorobutanesulphonyl) —SO$_2$—C$_4$F$_9$; or
tresyl groups (2,2,2-trifluoroethanesulphonyl) —SO$_2$—CH$_2$—CF$_3$.

26. The process according to claim 12, wherein the sulphonylating agent is:
triflic anhydride;
methanesulphonyl chloride;
trifluormethanesulphonyl chloride;
benzenesulphonyl chloride; or
p-toluenesulphonyl chloride.

27. The process according to claim 1, wherein the reaction between the hydroxylated compound and the sulphonylating agent is carried out in a liquid phase, optionally in the presence of an organic solvent.

28. The process according to claim 27, wherein the solvent is an aprotic or low polarity organic solvent.

29. The process according to claim 1, wherein the sulphonylating agent and the hydroxylating agent are in a molar ratio in a range of 0.9 to 2.

30. The process according to claim 29, wherein the molar ratio is in a range of 1.0 to 1.2.

31. The process according to claim 1, wherein the lewis acid is in a quantity representing 0.1% to 2% of the weight of the hydroxylated compound employed.

32. The process according to claim 1, wherein the sulphonylation reaction is carried out at a temperature in the range 20° C. to 150° C.

33. The process according to claim 12, wherein the sulphonylating agent and the Lewis acid are charged and the reaction mixture is stirred and heated to the desired temperature, and, then, the hydroxylated compound is added.

34. The process according to claim 16, wherein a sulphonylated compound with the following formula (III) is obtained:

wherein R$_1$ represents a hydrocarbon group substituted with at least one electron-attracting group (G), containing 1 to 40 carbon atoms, which is a linear or branched, saturated or unsaturated acyclic aliphatic group; a monocyclic or polycyclic, saturated or unsaturated or aromatic carbocyclic or heterocyclic group; or a concatenation of said groups; and R$_4$ represents a hydrocarbon group containing 1 to 20 carbon atoms.

35. The process according to claim 12, wherein 2,2,2-trifluoroethylmethanesulphonate is obtained from 2,2,2-trifluoroethanol and mesyl chloride, in the presence of antimony (V) chloride.

36. The process according to claim 1, wherein 2,2,2-trifluoroethylmethanesulphonate is obtained from 2,2,2-trifluoroethanol and mesyl chloride, in the presence of antimony (V) chloride.

* * * * *